(12) United States Patent
Fujii et al.

(10) Patent No.: US 7,167,737 B2
(45) Date of Patent: Jan. 23, 2007

(54) HEART RATE MONITORING UNIT

(75) Inventors: Kazuhiro Fujii, Osaka (JP); Toshikuni Suzuki, Osaka (JP); Hiroaki Shiraishi, Osaka (JP); Yoshinori Irie, Osaka (JP)

(73) Assignee: Shimano Inc. (JP)

( * ) Notice: Subject to any disclaimer, the term of this patent is extended or adjusted under 35 U.S.C. 154(b) by 256 days.

(21) Appl. No.: 11/028,876

(22) Filed: Jan. 3, 2005

(65) Prior Publication Data

US 2006/0149158 A1 Jul. 6, 2006

(51) Int. Cl.
*A61B 5/04* (2006.01)
(52) U.S. Cl. ...................... 600/390; 600/386
(58) Field of Classification Search ............... 600/386, 600/390
See application file for complete search history.

(56) References Cited

U.S. PATENT DOCUMENTS

| | | | |
|---|---|---|---|
| 6,272,365 B1 | 8/2001 | Ronkainen et al. | 600/390 |
| 6,553,247 B1 | 4/2003 | Rytky | 600/386 |
| D492,783 S | 7/2004 | Lax | D24/167 |
| 6,775,566 B2 | 8/2004 | Nissilä | 600/382 |
| 2002/0147410 A1* | 10/2002 | Bartholome | 600/519 |

FOREIGN PATENT DOCUMENTS

JP 51-033439 3/1976
JP 05-058590 A 9/1993

OTHER PUBLICATIONS 5 attached photographs A-E of a heart rate monitoring unit produced by Echowell of Taiwan.
2 attached photographs F and G of Polar Wearlink™ 31 Coded Transmitter Belt.
1 attached photograph H of a heart rate monitoring unit produced by Cardiosport.

* cited by examiner

*Primary Examiner*—Robert Pezzuto
*Assistant Examiner*—Yun Haeng Lee
(74) *Attorney, Agent, or Firm*—Jeffer Mangels Butler & Marmaro, LLP (57) ABSTRACT

A heart rate monitoring unit including a heart rate monitor and a belt. The heart rate monitor includes a base having a length defining a longitudinal axis, an electronics unit portion, a first electrode portion, and a first belt connection portion. The electronics unit portion has a first end proximate the first electrode portion and a second end distal from the first electrode portion. The first electrode portion has a first end proximate the electronics unit portion and a second end distal from the electronics unit portion. The first belt connection portion is disposed between the second end of the electronics unit portion and the second end of first electrode portion. The base includes a first electrode secured to the first electrode portion, and an electronics unit secured to the electronics unit portion.

28 Claims, 7 Drawing Sheets

HEART RATE MONITORING UNIT

FIELD OF THE INVENTION

The present invention relates generally to heart rate monitors, and more particularly, to heart rate monitors that include a circumferential belt for affixing the heart rate monitor to a user's chest.

BACKGROUND OF THE INVENTION

It is common to monitor a person's heart rate both for exercise or for other medical reasons. Many heart rate monitors are worn on a person's chest and are held in place using a belt that is wrapped around the person's torso. The heart rate monitors typically include a pair of electrodes that must remain in contact with the user's skin in order to receive the heart rate signal. However, the heart rate monitor unit and electrodes are typically encased in a hard plastic cover. The plastic cover does not usually fit well against the user's chest. As a result, during rigorous exercise, such as running, cycling or jogging, the electrodes often lose contact with the user's skin.

Thus, a need has arisen for a heart rate monitor that allows the electrodes to remain in contact with the user's skin even during rigorous exercise.

SUMMARY OF THE PREFERRED EMBODIMENTS

In accordance with a first aspect of the present invention, there is provided a heart rate monitor that comprises at least one electrode, an electronics unit in electrical communication with the at least one electrode, and a base. The electronics unit and the at least one electrode are supported by the base. The base includes a first bridging portion defined between the electronics unit and the at least one electrode. The first bridging portion includes at least one belt connection portion. In a preferred embodiment, the at least one electrode includes first and second electrodes, the base has a length defining a longitudinal axis, the electronics unit is disposed between the first and second electrodes along the longitudinal axis, the first bridging portion is defined between the first electrode and electronics unit, and the base further includes a second bridging portion defined between the second electrode and the electronics unit.

In accordance with another aspect of the present invention there is provided a heart rate monitor base that includes first and second electrode portions, an electronics unit portion disposed between the first and second electrode portions, and a first bridging portion defined between the first electrode portion and the electronics unit portion and a second bridging portion is defined between the second electrode portion and the electronics unit portion. The first bridging portion includes a first belt connection portion and the second bridging portion includes a second belt connection portion.

In accordance with another aspect of the present invention, there is provided a heart rate monitoring unit that includes a heart rate monitor and a belt. The heart rate monitor includes a base that is conformable to a user's chest and has a length defining a longitudinal axis, an electronics unit supported by the base, and first and second electrodes that are also supported by the base. The electronics unit is disposed between the first and second electrodes along the longitudinal axis, and the first and second electrodes are in electrical communication with the electronics unit. The base includes a first bridging portion defined between the electronics unit and the first electrode and a second bridging portion defined between the electronics unit and the second electrode. The first and second bridging portions have first and second openings defined therein, respectively, and the first and second openings each have a notch defined therein. The belt has first and second opposite ends that include first and second belt connectors, respectively. The first and second belt connectors each include a cylindrical portion having a flange extending therefrom. The cylindrical portion of the first belt connector is received by the first opening notch and the cylindrical portion of the second belt connector is received by the second opening notch.

In accordance with yet another aspect of the present invention, there is provided a heart rate monitor base having a length defining a longitudinal axis. The base includes an electronics unit portion, a first electrode portion, and a first belt connection portion. The electronics unit portion has a first end proximate the first electrode portion and a second end distal from the first electrode portion. The first electrode portion has a first end proximate the electronics unit portion and a second end distal from the electronics unit portion. The first belt connection portion is disposed between the second end of the electronics unit portion and the second end of first electrode portion. In a preferred embodiment, the heart rate monitor base further includes a second electrode portion having a first end proximate the second end of the electronics unit portion and a second end distal from the electronics unit portion, and a second belt connection portion disposed between the first end of the electronics unit portion and the second end of the second electrode portion. In this embodiment, the second belt connection portion projects away from the electronics unit portion.

In another preferred embodiment, the heart rate monitor base includes a first electrode secured to the first electrode portion, and an electronics unit secured to the electronics unit portion, thereby providing a heart rate monitor.

In another preferred embodiment, the heart rate monitor described above includes a belt having first and second ends. The first end of the belt is connected to the first belt connection portion, thereby providing a heart rate monitoring unit.

In other preferred embodiments of the heart rate monitoring unit, the second ends of the first and second electrode portions are each connected to the belt at a point between the first and second opposite ends of the belt, the base is made of a flexible rubber, at least a portion of the first belt connection portion overlaps with at least a portion of the first electrode portion along the longitudinal axis, at least a portion of the second belt connection portion overlaps with at least a portion of the second electrode portion along the longitudinal axis, and the first and second electrode portions are pivotable with respect to the electronics unit portion and the first and second belt connection portions, respectively.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
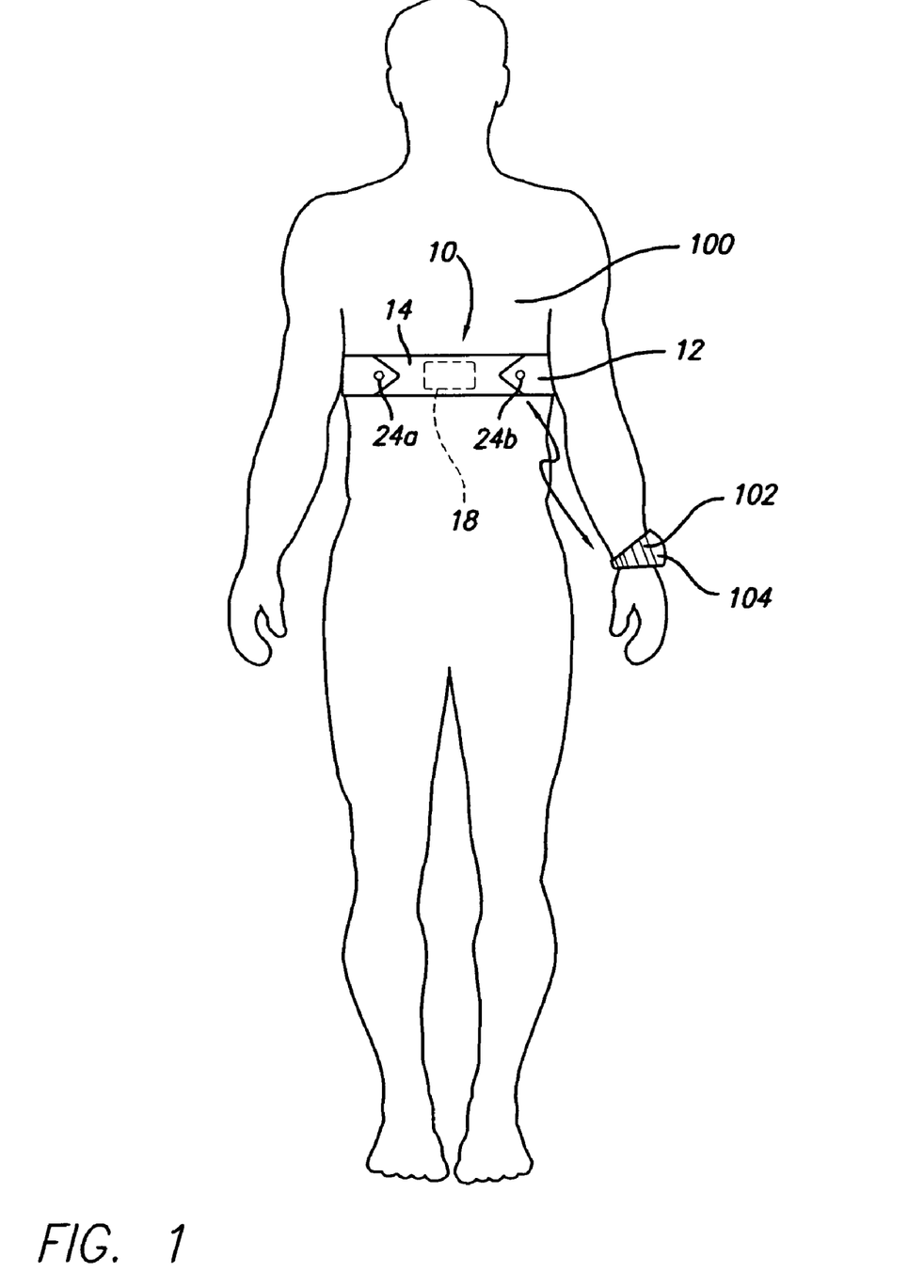
FIG. 1 is a an elevational view showing a heart rate monitoring unit including a heart rate monitor and belt secured on a person's chest in accordance with a first preferred embodiment of the present invention.
Figure 2:
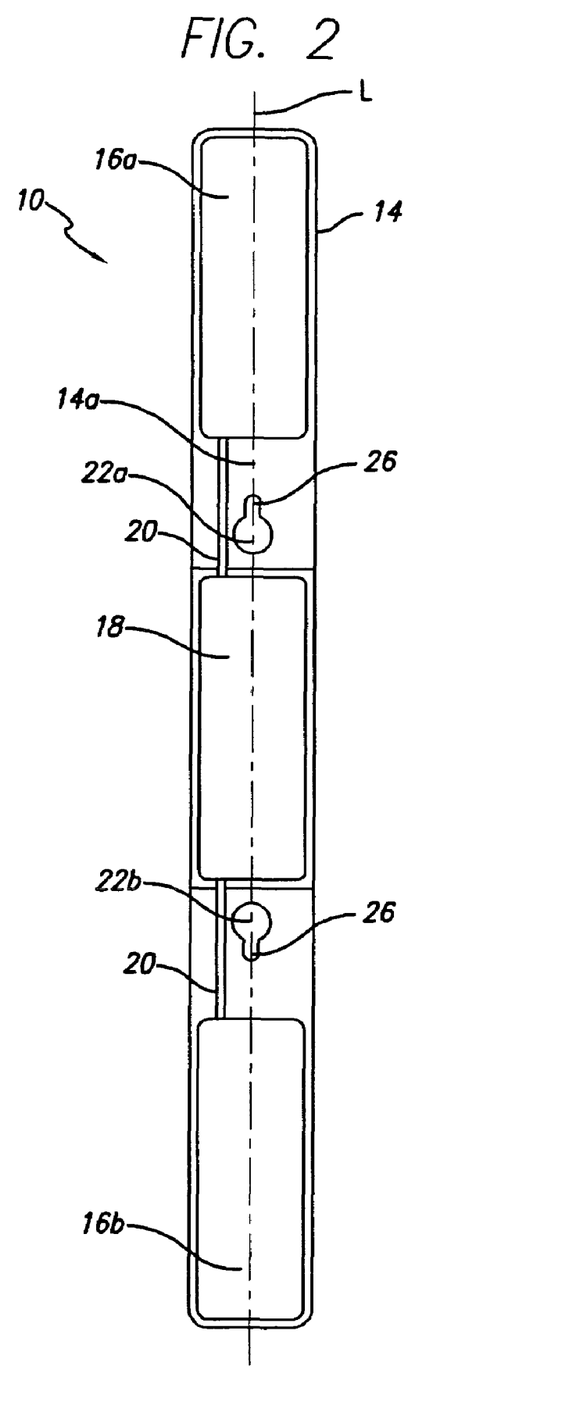
FIG. 2 is a bottom elevational view of the heart rate monitor of FIG. 1 showing the underside of the base and its components.

Referring to FIG. 1, a person (also referred to as a user) 100 wearing a heart rate monitor 10 is shown. The heart rate monitor 10 is held in place by a belt 12. With reference to FIG. 2, the heart rate monitor 10 includes a base 14 that includes at least one and preferably two or more electrodes 16a and 16b and an electronics unit 18. The user's heart rate is measured by the electrodes 16a and 16b. A measurable potential difference is formed between the two electrodes 16a and 16b as the heart beats.

The heart rate monitor 10 is fastened around the user's body by the belt 12, which is preferably made of an elastic material. The belt 12 can be made of a cloth, plastic or other elastomer, for example. The belt 12 can be any article for securing the base 14 to the user's body 100. For example, the belt can be a strap, cord, rope, strip or the like. In an alternative embodiment, the heart rate monitor 10 can be adhered to the user's body 100 using a temporary adhesive. As shown in FIG. 1, the measured heart rate information is transmitted inductively, for instance, to a receiver 102 comprising means 104 for displaying the measured heart rate. The receiver 102 can be located on the user's wrist, on a bicycle the user is riding or in any other advantageous location for the user to read the measured heart rate. Alternatively, the heart rate monitor 10 can include means for storing, processing and displaying the pulse information, thereby making a separate receiver 102 unnecessary.

Figure 3:
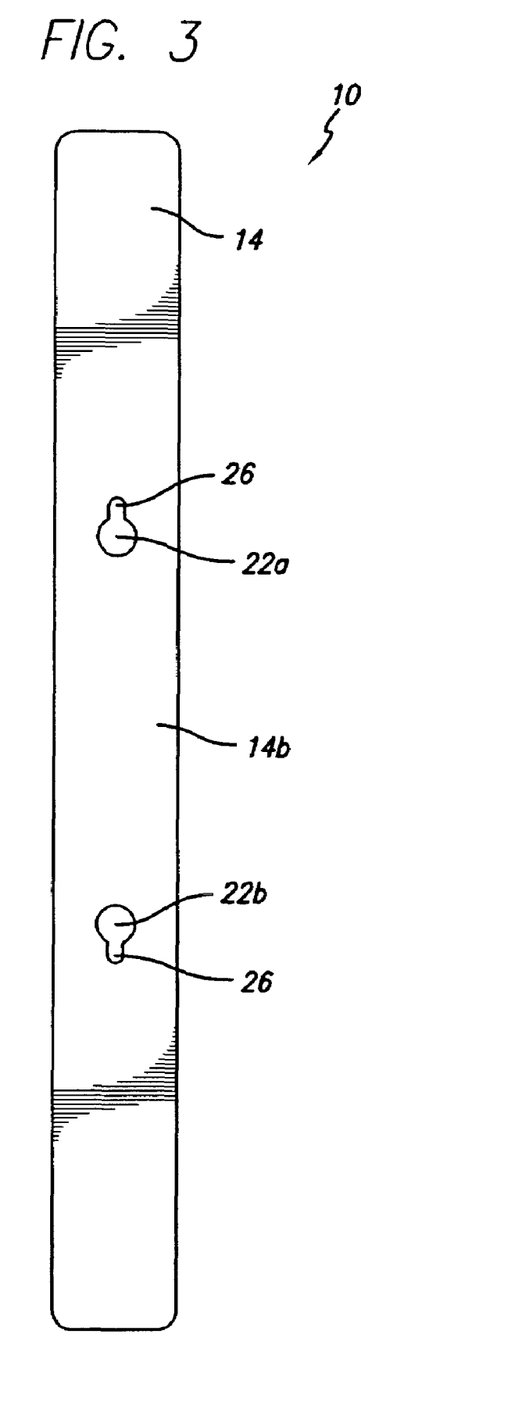
FIG. 3 is a top elevational view of the heart rate monitor of FIG. 1 showing the top surface of the base.

With reference to FIGS. 2 and 3, the base 14 of the heart rate monitor 10 includes two electrodes 16a, 16b. The electrodes 16a and 16b are located on the underside 14a of the base 14. In this position, the electrodes 16a and 16b will contact the user's skin when the heart rate monitor 10 is fitted on the user. It will be understood that the electrodes 16a and 16b can be secured to the base 14 in a number of different ways. For example, the electrodes 16a and 16b can be adhered to the base 14 or disposed in an opening in the base 14 or can be press fit therein.

As shown in FIG. 2, the base 14 also includes an electronics unit 18 disposed between the two electrodes 16a, 16b. The electronics unit 18 is in electrical communication with the two electrodes 16, 16b via conductors 20. The electronics unit 18 processes the information obtained from the electrodes 16a, 16b. The electronics unit 18 includes, for example, means for receiving a signal from the electrodes 16a and 16b, means for detecting heart rate from the received signal, means for storing heart rate information and means for transmitting the heart rate information inductively to the receiver 102. It should be understood that the operation of the electronics unit 18 is only exemplary and those skilled in the art will readily understand the operation of the electronics unit 18 and its interaction with the accompanying electrodes 16a and 16b. It will be understood that the electronics unit 18 can be secured to the base 14 in a number of different ways. For example, the electronics unit 18 can be adhered to the base 14 or in an opening in the base 14 or can be press fit therein. Furthermore, in a preferred embodiment, the base 14 is hollow and the electronics unit 18 is disposed therein.

The base 14 is preferably made from an elastomeric material, such as a rubber, that is flexible and allows the base 14 to give and flex during use. The base 14 can also made of plastic or other material. However, the materials of which the different components of the invention are made is not a limitation on the present invention.

Figure 4:
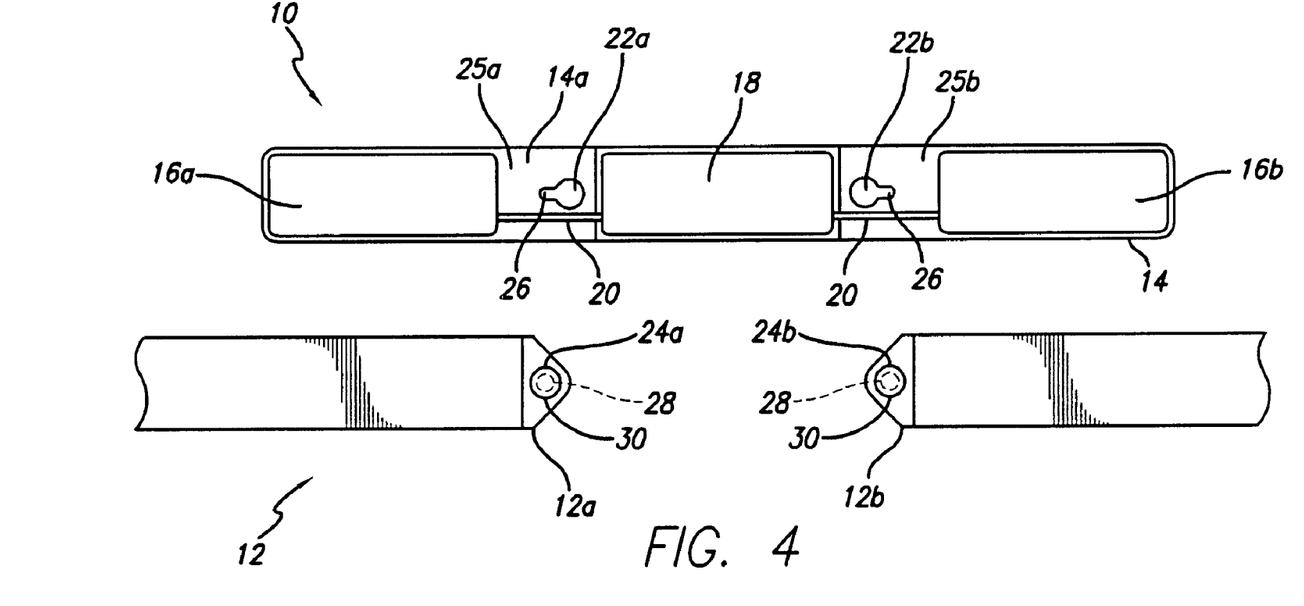
FIG. 4 is an exploded view of the heart rate monitor of FIG. 1 and the belt.
Figure 5:
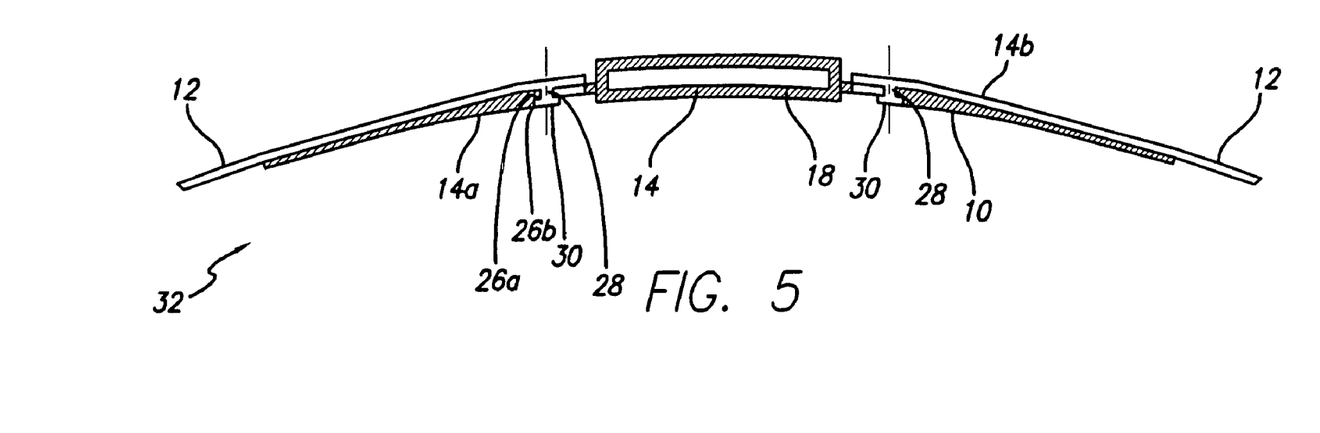
FIG. 5 is a side elevational view of the heart rate monitoring unit of FIG. 1, showing the base in cross-section.

As shown in FIGS. 4 and 5, the base 14 includes at least one and preferably two belt connection portions 22a and 22b and the belt 12 includes at least one and preferably two belt connectors 24a and 24b, respectively. A connection between the base 14 and the belt 12 can be implemented by any connection arrangement according to the invention, whereby the ends of the belt 12 and the base 14 are detachably connectable or they are fixedly connected together. However, as shown in the figures, in a preferred embodiment, the two belt connectors 24a and 24b on the opposite ends 12a and 12b of the belt 12 connect respectively to the belt connection portions 22a and 22b.

In a preferred embodiment, the belt connection portions 22a and 22b are disposed on bridging portions 25a and 25b. Bridging portions 25a and 25b are the portion of base 14 defined between the electronics unit 18 and the electrodes 16a and 16b, respectively. As shown in the FIG. 4, belt connection portion 22a is included in bridging portion 25a between the electronics unit 18 and electrode 16a and belt connection portion 22b is disposed on bridging portion 25b between electronics unit 18 and electrode 16b.

In a preferred embodiment, the belt connection portions are connection openings 22a and 22b that are defined in bridging portions 25a and 25b. Preferably, each of the connection openings 22a and 22b include a notch 26. The belt connectors 24a and 24b include a cylindrical portion 28 having a disc-like portion or flange 30 extending therefrom. To connect the heart rate monitor 10 to the belt 12, the flange 30 and cylindrical portion 28 of the belt connectors 24a and 24b are inserted into the connection openings 22a, 22b, respectively. Then the belt connectors 24a and 24b are moved into the notches 26 in a direction substantially parallel to the longitudinal axis L of the base 14, as shown in FIG. 2. The cylindrical portion 28 is then received by the notch 26. It will be understood that the connection openings 22a and 22b have a diameter larger than the flanges 30 and the notches 26 have a diameter smaller than the flanges 30.

This allows the belt connector 24 to be received in the connection opening 22 and then secured in the notch 26.

When fitted around a user's body, the elasticity of the belt 12 helps the belt connectors 24a and 24b remain secure in the notches 26. The force directed from the body outwards, which causes the elastic belt 12 to stretch, benefits the connection by making the cylindrical portions 28 of the belt connectors 24a and 24b press against the surfaces defining the notches 26.

In a preferred embodiment, as shown in FIG. 5, the connection openings 22a and 22b include a first notch 26a for receiving the cylindrical portion 28 and a second notch 26b for receiving the flange 30. This allows the flange 30 to be flush with the underside 14a of the base 14.

In another embodiment, the arrangement of the connection openings 22a and 22b and cylindrical portion 28 and flanges 30 can be reversed. The connection openings can be defined in the belt 12 and the cylindrical portions 28 and flanges 30 can be disposed on the bridging portions 25a and 25b. It will be understood that the belt connection portions 22a and 22b and the belt connectors 24a and 24b can comprise any known connection solution. For example, the belt connection portions 22a and 22b and the belt connectors 24a and 24b may comprise buttons, snaps, buckles or the like.

Due to the placement of the belt connection portions 22a and 22b inboard of the electrodes 16a and 16b, when the belt 12 is connected to the heart rate monitor 10 and the entire heart rate monitoring unit 32 (the belt 12 plus the heart rate monitor 10) is fitted around a user's body, a portion of the belt 12 presses against the top surface 14b of the base 14. This arrangement helps secure the electrodes 16a and 16b against the user's body. This can be advantageous during rigorous exercise where the prior art heart rate monitors may have a tendency to lose contact between the electrodes and the user's body. As shown in FIG. 5, preferably the base 14 has an arcuate shape. This also helps keep the electrodes 16a and 16b remain in contact with the user's body.

Figure 6:
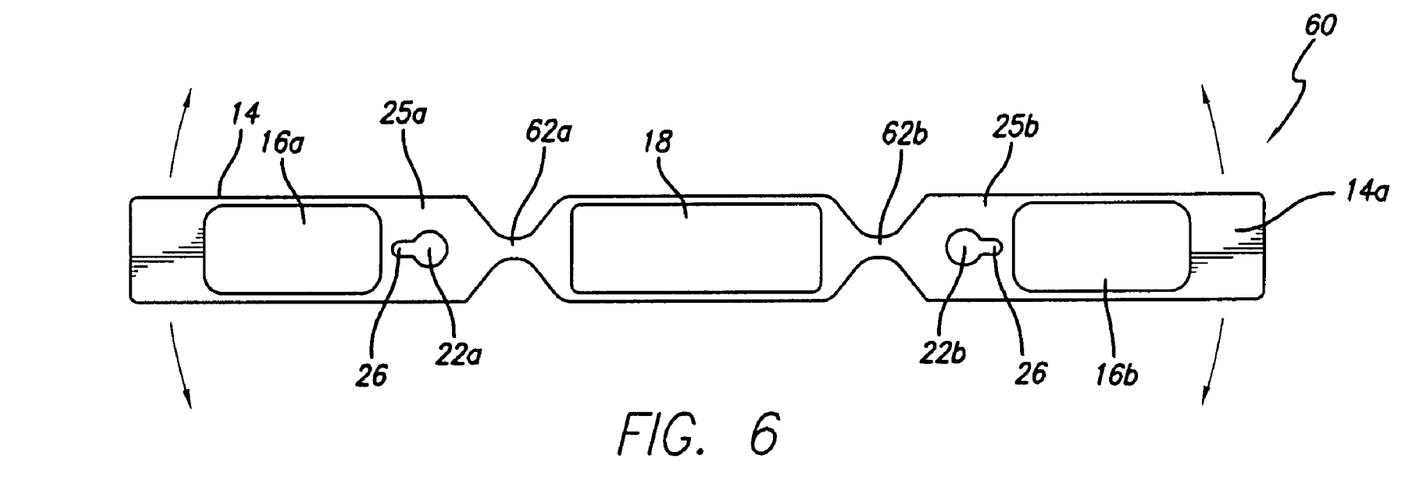
FIG. 6 is a bottom elevational view of a heart rate monitor having constricted portions in accordance with a second preferred embodiment of the present invention.
Figure 7:
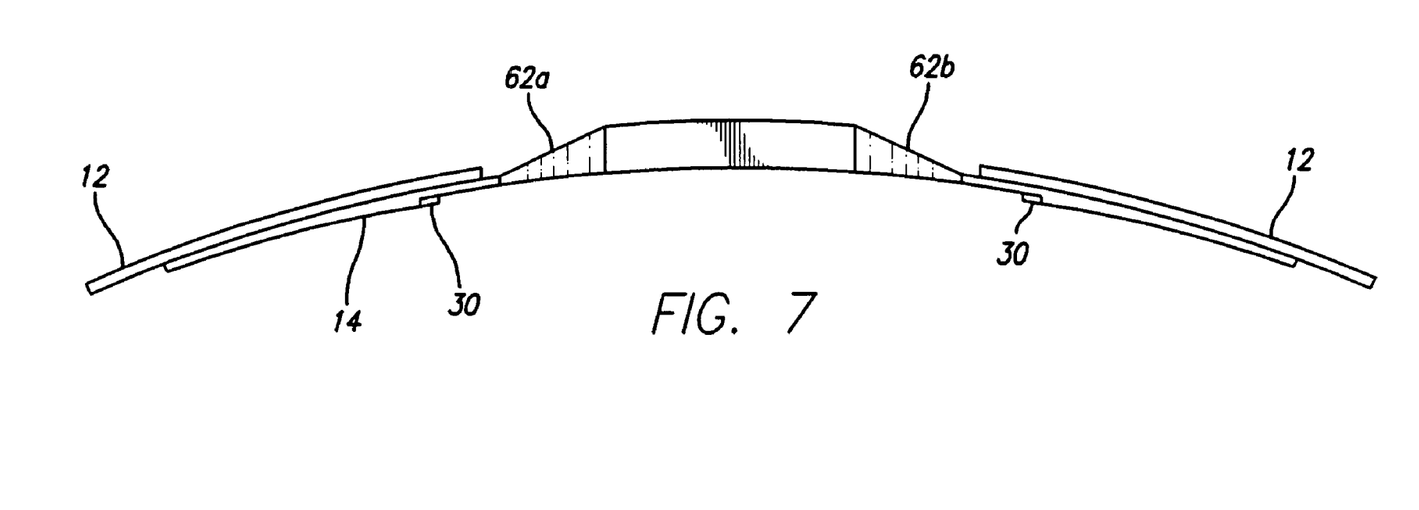
FIG. 7 is a side elevational view of the heart rate monitor of FIG. 6.

A second preferred embodiment of a heart rate monitor 60 of the present invention is shown in FIGS. 6 and 7. In accordance with this embodiment, the base 14 includes constricted portions 62a and 62b disposed between the electrodes 16a and 16b and the electronics unit 18. The constricted portions 62a and 62b are defined in the bridging portions 25a and 25b. As shown in FIG. 5, the electrodes 16a and 16b define a first width, the constricted portions 62a and 62b define a second width, and the first width is greater than the second width.

As described above, the base 14 is preferably made from an elastomeric material, such as a rubber, that is flexible and allows the base 14 to give and flex during use. The constricted portions 62a and 62b provide for even more flexibility. As will be appreciated by those skilled in the art, the constricted portions 62a and 62b allow the electrodes 16a and 16b to move in an up and down direction (see the arrows in FIG. 6) while a user is exercising. This feature allows the electrodes 16a and 16b to remain in contact with the user's body during rigorous exercise.

A third preferred embodiment of a heart rate monitor 70 of the present invention is shown in FIGS. 8–12. In this embodiment, the monitor 70 includes a base 72 having an electronics unit portion 74, belt connection portions 76a and 76b and electrode portions 78a and 78b. The electronics unit portion 74 has opposite ends 74a and 74b, electrode portion 78a has opposite ends 78c and 78d, and electrode portion 78b has opposite ends 78e and 78f. Furthermore, belt connection portion 76a has opposite ends 76c and 76d, and belt connection portion 76d has opposite ends 76e and 76f.

Figure 8:
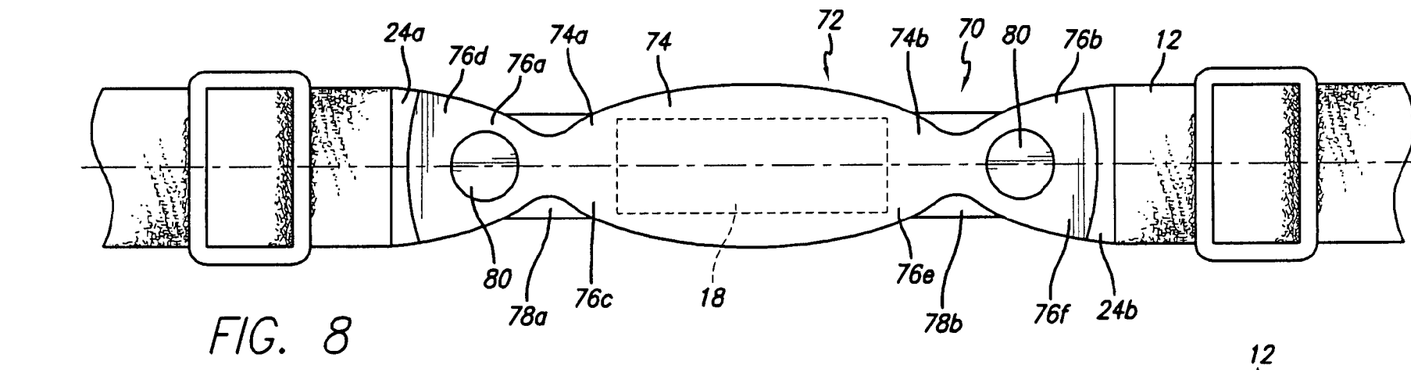
FIG. 8 is a top elevational view of a heart rate monitoring unit in accordance with a fifth preferred embodiment of the present invention.

As shown in FIG. 8, the electronics unit portion 74 includes an electronics unit 18 secured thereto. In a preferred embodiment, the electronics unit 18 is disposed inside the electronics unit portion 74. However, in other embodiments, the electronics unit 18 can be secured to the outside of the electronics unit portion 74. The electrode portions 78a and 78b include electrodes 16a and 16b secured thereto.

Figure 9:
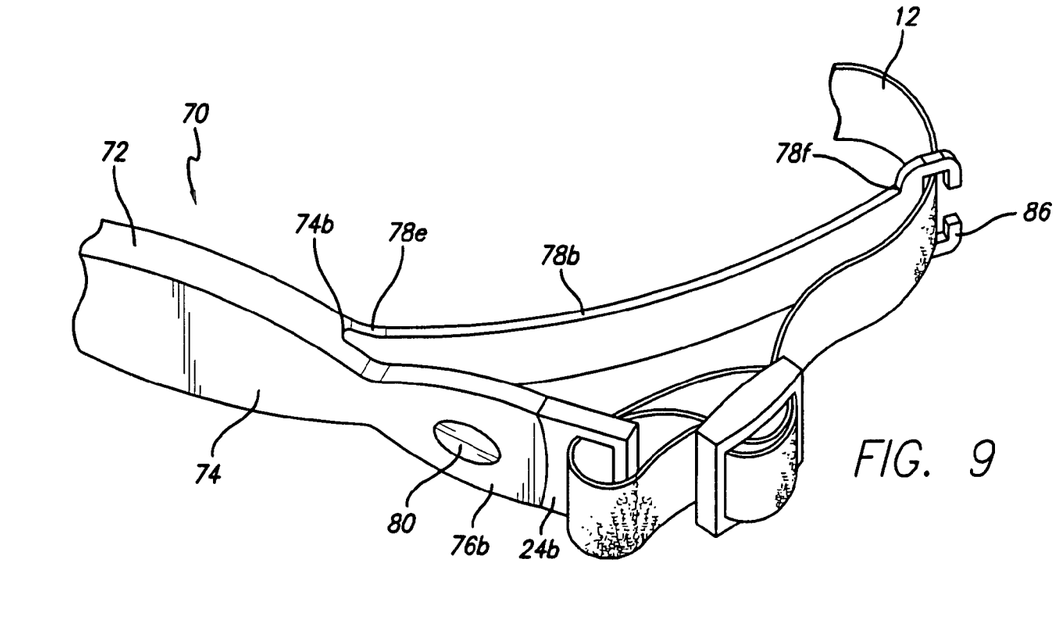
FIG. 9 is a perspective view of a portion of the heart rate monitoring unit of FIG. 8 showing the electrode portion pivoting away from the electronics unit portion and belt connection portion.
Figure 10:
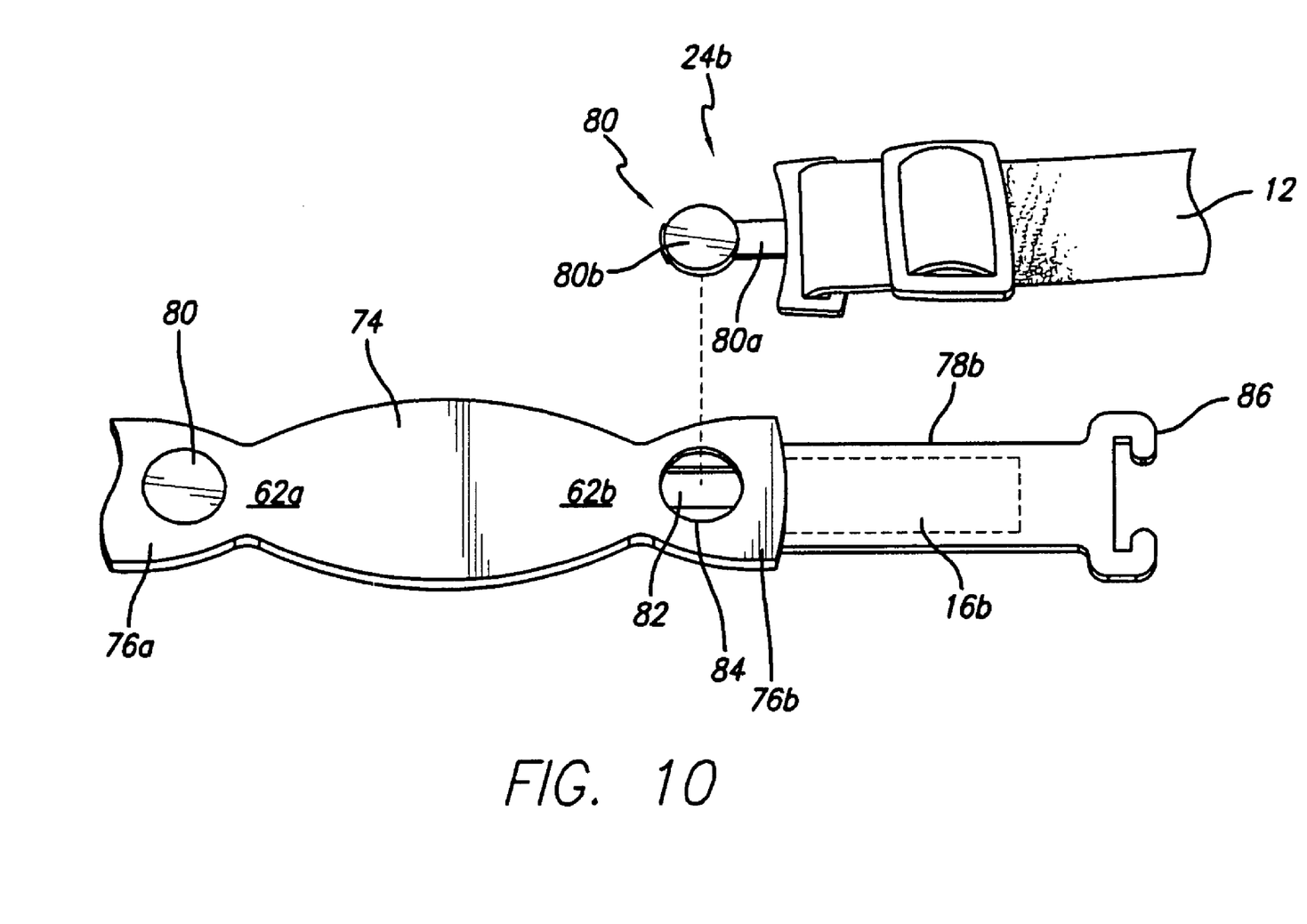
FIG. 10 is an exploded view of a portion of the heart rate monitoring unit of FIG. 8 showing how the belt connectors connect to the belt connection portion.
Figure 11:
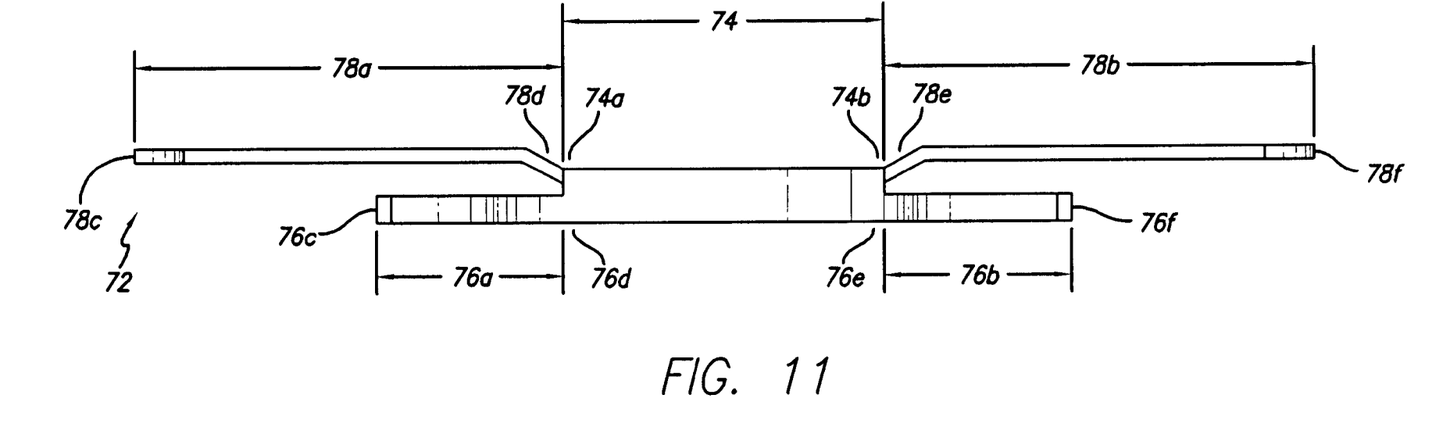
FIG. 11 is a side elevation view of the heart rate monitor base of FIG. 8 showing the electrode portions, belt connection portions, electronics unit portion, and their respective ends.

As is shown in FIG. 11, the distal ends 76c and 76f of the belt connection portions 76a and 76b extend away from the ends 74a and 74b of the electronics unit portion 74, as do the distal ends 78c and 78f of the electrode portions 78a and 78b. As shown in FIG. 8, the belt connection portions 76a and 76b overlap the electrode portions 78a and 78b along the longitudinal axis L. With this arrangement, when the belt 12 is connected to the heart rate monitor 70, the belt 12 holds the electrode portions 78a and 78b, and therefore, the electrodes 16a and 16b, against the user's body. As can be seen in FIG. 9, as a result of the thickness of the electrode portions 78a and 78b, the electrode portions 78a and 78b (only electrode portion 78b is shown) are pivotable with respect to the electronics unit portion 74 and the first and second belt connection portions 76a and 76b, respectively.

It will be understood that the presently described embodiment of the present invention anticipates belt connection portion 76a being disposed anywhere between end 74b of the electronics unit portion 74 and end 78c of electrode portion 76a. And, the present invention anticipates belt connection portion 76b being disposed anywhere between end 74a of the electronics unit portion 74 and end 78f of electrode portion 76b. In other words, the ends 76c and 76f of the belt connection portions 76a and 76b are positioned inboard of the ends 78c and 78f of the electrode portions 78a and 78b.

In a preferred embodiment, the belt connectors 24a and 24b of the belt 12 comprise slot-disc portions 80 (having an extension 80a and disc 80b) and the belt connection portions include corresponding casing slots 82 and openings 84. As will be understood by those skilled in the art, the slot-disc portions 80 are inserted into the casing slots 82, and the disc 84 is biased into the opening. This secures the belt 12 to the base 72. This arrangement is not a limitation on the present invention. It will be understood that any known connection or fastening solution is anticipated. For example, the belt connection portions 76a and 76b and the belt connectors 24a and 24b may comprise buttons, snaps, buckles or the like. Also, as is shown in the figures, the belt 12 may be adjustable.

Figure 12:
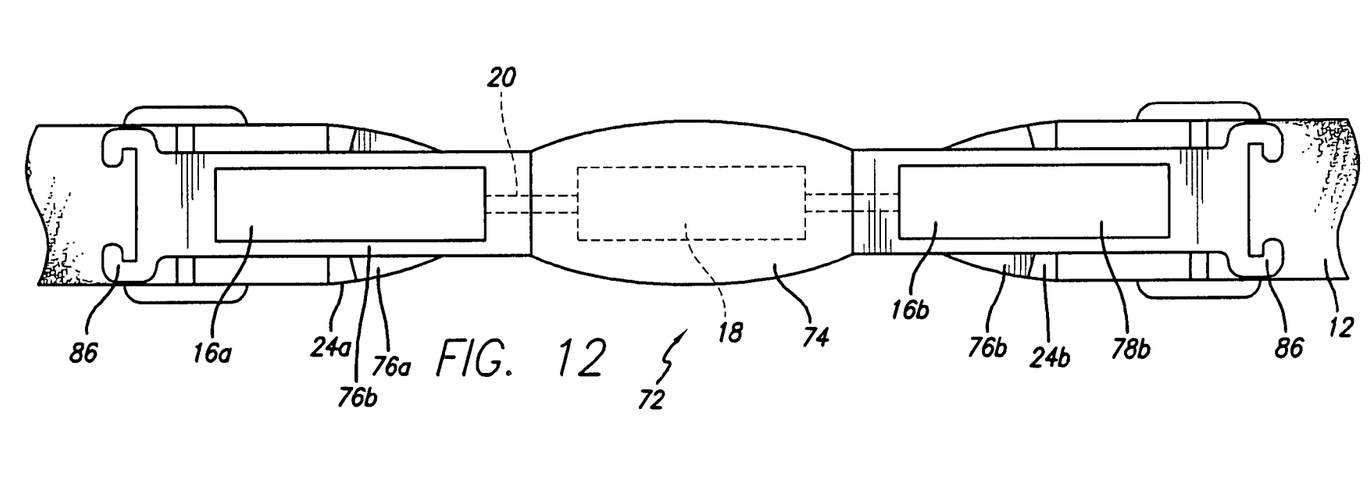
FIG. 12 is a bottom elevational view of the heart rate monitoring unit of FIG. 8.

As is shown in FIGS. 9 and 12, in a preferred embodiment, the electrode portions 78a and 78b (only 78b is shown in FIG. 9) include an adjustable engagement member 86 on the ends 78c and 78f thereof. The adjustable engagement members 86 each define a space 88 through which the belt 12 passes when the heart rate monitoring unit is secured to a user's body. The belt 12 can move within the space 88 during exercise. This arrangement helps hold the electrode portions 78a and 78b, and, therefore, the electrodes 16a and 16b against the user's body. Other connection solutions can also be included at the ends 78c and 78f of the electrode portions 78a and 78b. Other adjustable arrangements can be used, for example, the adjustable engagement member may define an enclosed space. Also, non adjustable arrangements, such as buttons, snaps, stitching or buckles can be used. Furthermore, the adjustable engagement members 86 can be omitted. As is shown in FIG. 11, this embodiment can also include constriction portions 62a and 62b.

The embodiments described above are exemplary embodiments of a the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A heart rate monitor comprising,
   first and second electrodes,
   an electronics unit, wherein the electronics unit is in electrical communication with the first and second electrodes, and
   a base having a length defining a longitudinal axis, wherein the electronics unit and the first and second electrodes are supported by the base and the electronics unit is disposed between the first and second electrodes along the longitudinal axis, the base includes first and second bridging portions defined between the electronics unit and the first electrode and the electronics unit and the second bridging portion, respectively, and the first bridging portion includes a first belt connection portion disposed thereon and the second bridging portion includes a second belt connection portion disposed thereon.

2. The heart rate monitor of claim 1 wherein the at least one belt connection portion comprises an opening defined in the first bridging portion and the opening includes a notch defined therein.

3. The heart rate monitor of claim 1 wherein the first and second belt connection portions comprise first and second openings defined in the first and second bridging portions, and wherein the first and second openings each include a notch defined therein.

4. The heart rate monitor of claim 1 wherein the base is conformable to a user's body part.

5. The heart rate monitor of claim 1 wherein the base has an arcuate shape.

6. The heart rate monitor of claim 1 wherein the first bridging portion includes a constricted portion.

7. The heart rate monitor of claim 6 wherein the at least one electrode defines a first width, the constricted portion defines a second width, and the first width is greater than the second width.

8. The heart rate monitor of claim 1 wherein the first and second bridging portions each include a constricted portion.

9. The heart rate monitor of claim 1 further comprising a belt having first and second opposite ends, wherein the first end includes a first belt connector and the second end includes a second belt connector, and the first and second belt connectors are coupled with the first and second belt connection portions, respectively.

10. The heart rate monitor of claim 9 wherein the first and second belt connection portions comprise first and second openings that each have a notch defined therein, and the first and second belt connectors each comprise a cylindrical portion having a flange extending therefrom, and
    wherein the cylindrical portion of the first belt connector is received by the first opening notch and the cylindrical portion of the second belt connector is received by the second opening notch.

11. The heart rate monitor of claim 9 wherein the first and second belt connection portions each comprise a cylindrical portion having a flange extending therefrom, and the first and second belt connectors comprise first and second openings that each have a notch defined therein, and
    wherein the cylindrical portion of the first belt connection portion is received by the first opening notch and the cylindrical portion at the second belt connection portion is received by the second opening notch.

12. The heart rate monitor of claim 1 wherein the heart rate monitor is secured to a user's body by a belt, the belt includes at least one bell connector that is coupled to the at least one belt connection portion of the base, and the at least one electrode is positioned between the belt and the user's body.

13. A heart rate monitor base comprising,
    first and second electrode portions,
    an electronics unit portion disposed between the first and second electrode portions, wherein a first bridging portion is defined between the first electrode portion and the electronics unit portion and a second bridging portion is defined between the second electrode portion and the electronics unit portion, and
    wherein the first bridging portion includes a first belt connection portion and the second bridging portion includes a second belt connection portion.

14. A heart rate monitoring unit comprising,
    a. a heart rate monitor, the heart rate monitor including
       i. a base, wherein the base has a length defining a longitudinal axis, and is conformable to a user's chest,
       ii. an electronics unit, wherein the electronics unit is supported by the base,
       iii. first and second electrodes, wherein the first and second electrodes are supported by the base, the electronics unit is disposed between the first and second electrodes along the longitudinal axis, and the first and second electrodes are in electrical communication with the electronics unit, and
       iv. wherein base includes a first bridging portior defined between the electronics unit and the first electrode and a second bridging portion defined between the electronics unit and the second electrode, the first and second bridging portions have first and second openings defined therein, respectively, and the first and second openings each have a notch defined therein, and
    b. a belt having first and second opposite ends, wherein the first end includes a first belt connector and the second end includes a second belt connector,
       i. wherein the first and second belt connectors each include a cylindrical portion having a flange extending therefrom, and
       ii. wherein the cylindrical portion of the first belt connector is received by the first opening notch and the cylindrical portion of the second belt connector is received by the second opening notch.

15. A heart rate monitor base having a length defining a longitudinal axis, the base comprising:
    a. an electronics unit portion,
    b. first and second electrode portions, and
    c. first and second belt connection portions, wherein the electronics unit portion has a first end proximate the first electrode portion and a second end distal from the first electrode portion, the first electrode portion has a first end proximate the electronics unit portion and a second end distal from the electronics unit portion, the second electrode portion has a first end proximate the second end of the electronics unit portion and a second end distal from the electronics unit portion, the first belt connection portion is disposed between the second end of the electronics unit portion and the second end of first electrode portion, and the second belt connection portion disposed between the first end of the electronics unit portion and the second end of the second electrode portion, wherein the second belt connection portion projects away from the electronics unit portion.

16. A heart rate monitor comprising:
the heart rate monitor base of claim 15,
a first electrode secured to the first electrode portion, and
an electronics unit secured to the electronics unit portion.

17. A heart rate monitoring unit, comprising:
a. the heart rate monitor of claim 16, and
b. a belt having first and second ends, wherein the first end of the belt is connected to the first belt connection portion.

18. The heart rate monitoring unit of claim 17 wherein the belt overlaps the first electrode portion.

19. A heart rate monitor comprising:
the heart rate monitor base of claim 15,
a first electrode secured to the first electrode portion,
a second electrode secured to the second electrode portion, and
an electronics unit secured to the electronics unit portion.

20. A heart rate monitoring unit, comprising:
a. The heart rate monitor base of claim 19; and
b. a belt having first and second ends, wherein the first end of the belt is connected to the first belt connection portion, and the second end of the belt is connected to the second belt connection portion.

21. The heart rate monitoring unit of claim 20 wherein at least a portion of the first belt connection portion overlaps with at least a portion of the first electrode portion along the longitudinal axis, and at least a portion of the second belt connection portion overlaps with at least a portion of the second electrode portion along the longitudinal axis, and
wherein the second ends of the first and second electrode portions are each connected to the belt at a point between the first and second opposite ends of the belt.

22. The heart rate monitoring unit of claim 21 wherein the second ends of the first and second electrode portions are adjustably connected to the belt.

23. The heart rate monitoring unit of claim 20 wherein the first and second ends of the belt include first and second belt connectors, respectively, and the first and second belt connectors are connected to the first and second belt connection portions of the base, respectively.

24. The heart rate monitoring unit of claim 23 wherein the first and second belt connectors each comprise a disc, and the first and second belt connection portions each comprise an opening defined therein for receiving the discs of the first and second belt connectors.

25. The heart rate monitoring unit of claim 20 wherein the first and second electrode portions are pivotable with respect to the electronics unit portion and the first and second belt connection portions, respectively.

26. The heart rate monitor base of claim 15 wherein the base is comprised of a flexible rubber.

27. The heart rate monitor base of claim 15 wherein the first belt connection portion is secured to the electronics unit portion.

28. The heart rate monitoring base of claim 15 wherein the first belt connection portion overlaps the first electrode portion along the longitudinal axis.

* * * * *